US010946059B2

(12) United States Patent
Chaudhary et al.

(10) Patent No.: US 10,946,059 B2
(45) Date of Patent: Mar. 16, 2021

(54) FORMULATION CONTAINING AN EXTRACT OF ALPINIA GALANGA, A PROCESS FOR THE PREPARATION THEREOF, AND USES THEREOF

(71) Applicant: ENovate Biolife LLC, Wilmington, DE (US)

(72) Inventors: Jayesh Chaudhary, Mumbai (IN); Latha Chaudhary, Mumbai (IN); Sachin Dighe, Mumbai (IN); Shalini Srivastava, Mumbai (IN)

(73) Assignee: Enovate Biolife LLC, Wilmington, DE (US)

( * ) Notice: Subject to any disclaimer, the term of this patent is extended or adjusted under 35 U.S.C. 154(b) by 430 days.

(21) Appl. No.: 15/593,093

(22) Filed: May 11, 2017

(65) Prior Publication Data

US 2018/0221430 A1  Aug. 9, 2018

(30) Foreign Application Priority Data

Feb. 9, 2017  (IN) .............................. 201721004749

(51) Int. Cl.
*A61K 36/906* (2006.01)
*A61K 36/00* (2006.01)
*A61K 36/9062* (2006.01)
*A61K 31/522* (2006.01)

(52) U.S. Cl.
CPC ........ *A61K 36/9062* (2013.01); *A61K 31/522* (2013.01); *A61K 2236/15* (2013.01); *A61K 2236/331* (2013.01); *A61K 2236/51* (2013.01)

(58) Field of Classification Search
None
See application file for complete search history.

(56) References Cited

U.S. PATENT DOCUMENTS

| | | | |
|---|---|---|---|
| 7,252,845 B2 | 8/2007 | Weidner et al. | |
| 2007/0185141 A1* | 8/2007 | Patterson | .................. A61P 3/00 514/263.3 |
| 2008/0226786 A1* | 9/2008 | Ward | ...................... A23L 19/09 426/534 |
| 2016/0120930 A1* | 5/2016 | Giversen | ............ A61K 36/9062 424/756 |

FOREIGN PATENT DOCUMENTS

| | | | |
|---|---|---|---|
| IN | 200400386 | * | 5/2006 |
| JP | 2004-189669 | | 7/2004 |

OTHER PUBLICATIONS

Singh et al. (Neuroprotective effect of *Apinia galanga* (L.) fractions on Abeta(25-35) induced amnesia in mice, Journal of Ethnophamacology vol. 136, Issue 1, Oct. 31, 2011, pp. 85-91 or pp. 1-13) (Year: 2011).*
Galangal Shredded (50 grams) (Alpinia Galanga) Dec. 1, 2016, http://www.dutchheadshop.com/en/galangalshredded50gramsalpiniagalangap728.html.
Chan, Antioxidant and Antibacterial Properties of Appinia galanga, Curcuma longa and Etlingera elatior (Zingiberaceae), Pharmacognosy Journal, Jun. 2011, vol. 3, Issue 22.
Chan, et al., Effects of different drying methods on the antioxidant properties of leaves and tea of ginger species, Food Chemistry 113 (2009) 166-172.
Chudiwal, et al., Alpinia galanga Willd.—An Overview on Phytopharmacological properties, Indian Journal of Natural Products and Resources, vol. 1(2), Jun. 2010, pp. 143-149.
Ghosh, et al., Alpinia: the gold mine of future therapeutics, 3 Biotech (2013) 3:173-185.
Mayachiew, et al., Antimicrobial and antioxidant activities of Indian gooseberry and galangal extracts, Food Science and Technology 41 (2008) 1153-1159.
Saha, et al., Central nervous system stimulant actions of *Alpinia galanga* (L.) rhizome: A preliminary study, Indian Journal of Experimental Biology, vol. 51, Oct. 2013, pp. 828-832.
Victorio, Therapeutic value of the genus *Alpinia zingiberaceae*, Brazilian Journal of Pharmacognosy 21(1): 194-201, Jan./Feb. 2011.

* cited by examiner

*Primary Examiner* — Michael Barker
*Assistant Examiner* — Randall O Winston
(74) *Attorney, Agent, or Firm* — Kramer Amado

(57) ABSTRACT

Various embodiments relate to formulations containing an extract of *Alpinia galanga*; a method of improving cognitive performance by administering an extract of *Alpinia galanga*; and a process for preparing an extract of *Alpinia galanga*.

6 Claims, 2 Drawing Sheets

FORMULATION CONTAINING AN EXTRACT OF ALPINIA GALANGA, A PROCESS FOR THE PREPARATION THEREOF, AND USES THEREOF

TECHNICAL FIELD

This disclosure generally relates to an extract of *Alpinia galanga*. The embodiments further include a method for preparing an extract of *Alpinia galanga* and methods of administering an extract of *Alpinia galanga* to improve cognitive performance.

BACKGROUND

*Alpinia galanga* is a plant related to ginger and is found in various parts of Southeast Asia. It is used in cooking, particularly the rhizome of the plant. There are some folk medicine uses of *Alpinia galanga* for treating colds. Other uses of *Alpinia galanga* include treating pain, treating digestive ailments, and treating infections. The extract of *Alpinia galanga* rhizomes includes phenolic compounds and flavanoids.

Many people use stimulants such as caffeine, or energy drinks, to improve mental function, including improved attention. However, caffeine and energy drinks are known to have side effects such as a "crash," which results in a less-stimulated state as compared to before their consumption. Despite their side effects, caffeine and energy drinks are widely available and frequently used for their stimulant effect.

Various extraction and isolation processes may be used to substantially alter the characteristics and amounts of the chemical components of the naturally occurring plant. These processes may concentrate or remove various chemicals to form non-naturally occurring compositions. For example, *Alpinia galanga* extracts may be prepared using alcohol solvents.

In view of the foregoing, it would be desirable to provide a product that improves cognitive performance without side effects.

SUMMARY

In light of the present need for a product to improve cognitive performance and an aqueous extract of *Alpinia galanga*, a brief summary of various embodiments is presented. Some simplifications and omissions may be made in the following summary, which is intended to highlight and introduce some aspects of the various embodiments, but not to limit the scope of the disclosed formulation, extraction process, and use. Detailed descriptions of embodiments adequate to allow those of ordinary skill in the art to make and use the inventive concepts will follow in later sections.

Various embodiments relate to a formulation that includes an effective amount of an extract of *Alpinia galanga* that is free of methyl eugenol; a method of improving cognitive performance by administering a formulation containing an effective amount of an extract of *Aplinia galanga* that is free of methyl eugenol; and processes for preparing an extract of *Alpinia galanga* that is free of methyl eugenol.

The formulation may be in the form of commonly used formulations, including, but not limited to: a tablet, a capsule, a lozenge, a film, a powder, a sustained release formulation, a liquid formulation, a parenteral formulation, an inhaled formulation, a lyophilized formulation, a suppository, and a topical formulation. The formulation may also include commonly used nutraceutical dosage forms, including, but not limited to: functional foods and beverages, energy shots, energy bars, energy drinks, and performance supplements. The formulation may further include an excipient, such as a pharmaceutically acceptable excipient. In some embodiments, the formulation includes an effective amount of an extract of *Alpinia galanga* that is free of methyl eugenol and has a ratio of polyphenols to polysaccharides of about 1:1.6 to about 1:6. In another aspect, the ratio of polyphenols to polysaccharides is about 1:1.6 to about 1:2.2. In another aspect, the ratio of polyphenols to polysaccharides is about 1:5 to about 1:6. In another aspect, the ratio of polyphenols of polysaccharides is about 1:5 to about 1:12. In some embodiments, the formulation includes an effective amount of an extract of *Alpinia galanga* that is free of methyl eugenol and has 1% pyrocatecollic type tannins. In some embodiments, the formulation includes an effective amount of an extract of *Alpinia galanga* that is free of methyl eugenol and has not more than 100 ppm galangin. In some embodiments, the formulation includes 100-900 mg of an extract of *Alpinia galanga* that is free of methyl eugenol. In other embodiments, the formulation includes 300 mg of an extract of *Alpinia galanga* that is free of methyl eugenol.

In other embodiments, an effective amount of an extract of *Alpinia galanga* that is free of methyl eugenol is administered to a mammal to improve cognitive performance. In some embodiments, the effective amount of the extract of *Alpinia galanga* that is free of methyl eugenol is administered to a human. In some embodiments, administering the effective amount of the extract of *Alpinia galanga* that is free of methyl eugenol improves mental alertness, increases attention, decreases mean response time, decreases mental fatigue, improves sustained wakefulness, or any combinations of these effects. In one aspect, administering the effective amount of the extract of *Alpinia galanga* that is free of methyl eugenol in combination with caffeine impedes caffeine crash. Some embodiments include administering an effective amount of an extract of *Alpinia galanga* that is free of methyl eugenol and has a ratio of polyphenols to polysaccharides of about 1:1.6 to about 1:6. In another aspect, the ratio of polyphenols to polysaccharides is about 1:1.6 to about 1:2.2. In another aspect, the ratio of polyphenols to polysaccharides is about 1:5 to about 1:6. In another aspect, the ratio of polyphenols to polysaccharides is about 1:5 to about 1:12. Some embodiments include administering an effective amount of an extract of *Alpinia galanga* that is free of methyl eugenol and has 1% pyrocatecollic type tannins. Some embodiments include administering an effective amount of an extract of *Alpinia galanga* that is free of methyl eugenol and has not more than 100 ppm galangin. In some embodiments, the effective amount is 100-900 mg of an extract of *Alpinia galanga* that is free of methyl eugenol. In other embodiments, the effective amount is 300 mg of an extract of *Alpinia galanga* that is free of methyl eugenol.

Other embodiments include the preparation of an extract of *Alpinia galanga* that is free of methyl eugenol. In one embodiment, the process includes the steps of:

a) powdering and sieving the dried rhizome of *Alpinia galanga* to produce a product, b) extracting the product of Step a with an aqueous solvent to produce a product, c) concentrating the product of Step b under vacuum to produce a product, d) drying the product of Step c under vacuum to produce a product, e) pulverizing the product of Step d.

In some embodiments, the aqueous solution of Step b is added at four times the amount of the dried rhizome of Step a. In some embodiments, Step b further includes the step of soaking the product of Step a in water at 0-25° C. for 8-10 hours and also includes the steps of extracting for a cycle of 5-6 hours in an aqueous solvent at 70-80° C. and a pressure of 1-10 bars. In some embodiments, the process includes repeating the extraction for 5-6 hours at 70-80° C. for two additional cycles. In some embodiments, Step c is performed at 70-80° C., under vacuum. In some embodiments, Step d is performed at 80-90° C. and a vacuum pressure of 650 mm Hg for a period of 6-8 hours. In some embodiments, Step e includes pulverizing the product of Step d with silicon dioxide.

It should be apparent that, in this manner, various embodiments enable formulations containing an extract of *Alpinia galanga* that is free of methyl eugenol; methods of administering a formulation containing an extract of *Alpinia galanga* that is free of methyl eugenol to improve cognitive performance; and a process for preparing an extract of *Alpinia galanga* that is free of methyl eugenol.

DETAILED DESCRIPTION

Figure 1:
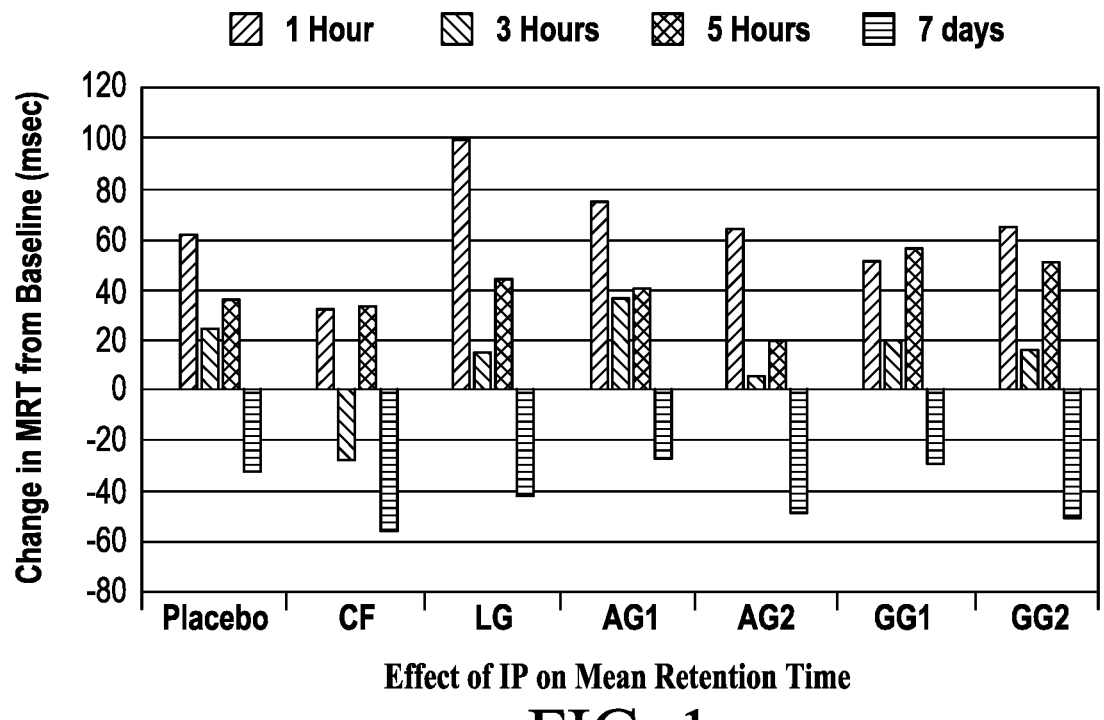
FIG. 1 shows an effect of an *Alpinia galanga* extract that is free of methyl eugenol and other extracts on Mean Response Time.

The first aspect of the disclosure is a formulation that includes an effective amount of an extract of *Alpinia galanga* that is free of methyl eugenol and a pharmaceutically acceptable excipient. The formulation may be any type of pharmaceutically acceptable formulation that is used to dose an active agent. Examples of pharmaceutically acceptable formulations include: tablets, capsules, lozenges, films, powders, sustained release formulations, liquid formulations, parenteral formulations, inhaled formulations, lyophilized formulations, suppositories, and topical formulations. In one embodiment, the formulations include oral dosage forms, i.e., tablets, capsules, and sustained release formulations. In another embodiment, the formulation is a capsule. In one aspect, the capsule may include granules of *Alpinia galanga* that is free of methyl eugenol and a granulating polymer.

The pharmaceutically acceptable excipient may be a binder, a diluent, a filler, a disintegrant, a lubricant, a glidant, a coating, a flavoring, a buffer, or combinations thereof. In one embodiment, the pharmaceutically acceptable excipient is microcrystalline cellulose. In another embodiment, the pharmaceutically acceptable excipient is maltodextrin.

The formulation may also include commonly used nutraceutical dosage forms, including, but not limited to: dietary and nutritional supplements, functional foods and beverages, energy shots, energy bars, energy drinks, performance supplements, and sports products.

In one embodiment, the effective amount of the extract of *Alpinia galanga* that is free of methyl eugenol is 300 mg. However, the safe and effective amount of the extract of *Alpinia galanga* that is free of methyl eugenol includes any amount that has the desired effect, i.e., improvement in cognitive performance. In other embodiments, the effective amount may include 100-900 mg of the extract of *Alpinia galanga* that is free of methyl eugenol.

In other embodiments, the extract of *Alpinia galanga* that is free of methyl eugenol may include one or more of the following characteristics: having a ratio of polyphenols to polysaccharides of about 1:1.6 to about 1:12; including 1% pyrocatecollic type tannins; including not more than 100 ppm galangin; or combinations of these characteristics.

The *Alpinia galanga* extract that is free of methyl eugenol includes polyphenolic compound and polysaccharides. In one embodiment, the ratio of polyphenols to polysaccharides is about 1:1.6. In another embodiment, the ratio of polyphenols to polysaccharides is about 1:2.2. In another embodiment, the ratio of polyphenols to polysaccharides is about 1:5. In another embodiment, the ratio of polyphenols to polysaccharides is about 1:6. In another embodiment, the ratio of polyphenols to polysaccharides is about 1:12. As discussed below, the process for extraction of *Alpinia galanga* that is free of methyl eugenol may be performed with cold water, i.e., water at a temperature of 0-25° C. In other embodiments, the extraction may be performed using hot water (e.g., 70° C. or 80° C.) or using methanol. The amounts of polyphenols and polysaccharides produced by each method are shown in Table 1 below:

TABLE 1

| Extraction Process | Polyphenols | Polysaccharides |
| --- | --- | --- |
| Hot water (70° C.) | 8.09% | 13.09% |
| Hot water (80° C.) | 7.19% | 16.13% |
| Cold water (0-25° C.) Batch 253 | 4.89% | 24.90% |
| Cold water (0-25° C.) batch 264 | 5.20% | 26.91% |
| Cold water (0-25° C.) batch 361 | 4.15% | 42.06% |
| Cold water (0-25° C.) batch 327 | 5.86% | 35.65% |
| Methanol | 3.23% | 38.34% |

As shown by these data, the ratio of polyphenols to polysaccharides is markedly different when cold water is used as the extraction solvent as compared to when hot water is used. In particular, the polyphenol content is relatively low while the polysaccharide content is significantly higher. Therefore, the ratio of about 1:5 is different using cold water as compared to a ratio of 1:1.6 or 1:2.2 using hot water. The use of methanol as an extraction solvent results in a ratio of 1:11.9. Accordingly, using cold water to extract *Alpinia galanga* results in a ratio of polyphenols to polysaccharides that is distinct from the ratio derived from using other methods.

In another embodiment, the extract of *Alpinia galanga* is free from methyl eugenol. In one aspect, the extract does not include any detectable amount of methyl eugenol. In another aspect, the extract includes less than 1 ppm of methyl eugenol. Methyl eugenol is a methyl ester of eugenol that may be found in some essential oils. It is also used as a flavoring, a fragrance, and an anesthetic in rodents. However, methyl eugenol has been found to be mutagenic in animals and therefore may be carcinogenic to humans. Accordingly, the *Alpinia galanga* extract is free of methyl eugenol.

In another embodiment, the extract of *Alpinia galanga* that is free of methyl eugenol has 1% pyrocatecollic type tannins. In another embodiment, the extract of *Alpinia galanga* that is free of methyl eugenol has not more than 100 ppm galangin.

In the second aspect of the disclosure, a formulation containing an effective amount of the extract of *Aplinia galanga* that is free of methyl eugenol is administered to improve cognitive performance. An improvement in cognitive performance includes, but is not limited to: improved mental alertness, increased attention, decreased mean response time, decreased mental fatigue, impeded caffeine crash, improved sustained wakefulness, and combinations thereof. Therefore, any administration of an effective amount of an extract of *Alpinia galanga* that is free of methyl eugenol that results in the foregoing effects, or similar effects, is encompassed by the present disclosure.

According to a study described below, in Example 1, the water-soluble extract of *Aplinia galanga* that is free of methyl eugenol shows increased improvement of cognitive performance as compared to a water-insoluble extract. The data further show the superiority of the water-soluble extract of *Alpinia galanga* that is free of methyl eugenol as compared to caffeine, placebo, and extracts of other herbs. The mean response time for subjects administered the water-soluble extract of *Alpinia galanga* that is free of methyl eugenol improved after one hour and after three hours. Further, the water-soluble extract of *Alpinia galanga* that is free of methyl eugenol improved alertness time after one hour and after three hours.

Without wishing to be bound by any theory, the Applicants believe that the components of the water-soluble extract of *Alpinia galanga* that is free of methyl eugenol are responsible for the beneficial results. In particular, polyphenols, polysaccharides, and pyrocatecollic type tannins are found in *Alpinia galanga*. The water-extraction method produced these compounds in ratios and amounts that are distinct from the naturally occurring powder or an alcoholic extraction. Therefore, the superior improvement of cognitive performance may be due to these components.

In another study described below, in Example 2, the effect of an extract of *Alpina galanga* that is free of methyl eugenol was compared to the effect of caffeine, a composite of an extract of *Alpinia galanga* that is free of methyl eugenol with caffeine, and placebo. The group administered the extract of *Alpinia galanga* that is free of methyl eugenol showed improved alertness after one hour, after three hours, and after five hours. The caffeine group showed improvement after one hour but then a reduction as compared to baseline after three hours. This indicates a "caffeine crash." The composite group showed an improvement after one hour and a return to baseline after three hours, indicating no crash. Therefore, administration of the extract of *Alpinia galanga* that is free of methyl eugenol in combination with caffeine impedes caffeine crash.

In a third aspect of the disclosure, water is used to extract *Alpinia galanga*. The extraction process is distinct from extractions using organic solvents. In one embodiment, cold (i.e., 0-25° C.) water is used to extract *Alpinia galanga*. This embodiment is distinct from extractions using hot water. The extraction process may include the steps of powdering and sieving the dried bark of *Alpinia galanga*. In one embodiment, the rhizome is used. The powder may then be extracted with an aqueous solution, including water. The extract may then be concentrated under vacuum and dried under a controlled temperature. The dried product is pulverized under a controlled temperature and humidity in order to obtain the extract.

In further embodiments, the aqueous solution is added at four times the amount of the dried rhizome. A first extraction cycle may be performed by soaking the dried rhizome in cold water (i.e., 0-25° C.) for 8 hours. In another embodiment, second, third and fourth extractions are performed for a period of 5-6 hours at temperature of 70-80° C. Without wishing to be bound by any theory, Applicants believe that using four extractions maximizes the recovery of the extracts from the dried rhizome. Additional extraction cycles may be used. The total number of extraction cycles are calculated based on the total dissolved solids in the extract. The collected extract is then distilled at 70-80° C. Distillation stopped after a syrupy material stops bubbling in the distillatory. The product may then be dried under vacuum at 80-90° C. and at a vacuum pressure of 650 mm for 6-8 hours. The dried product may then be pulverized with excipients like silicon dioxide under controlled temperature and humidity conditions, to obtain the desired powder product.

Example 1: Effect of the Water-Soluble Extract of *Alpinia galanga* that is Free of Methyl Eugenol as Compared to a Water-Insoluble Extract, Caffeine, and Other Herbs The following study compared the effects *Cymbopogon flexuosus* (lemongrass, LG), *Alpinia galanga* (AG1 and AG2), and *Glycyrrhiza glabra* (licorice, GG1 and GG2) on improving brain performance, mainly by enhancing attention network-related functioning.

Participants

Seventy subjects (male and female) between 18-40 years of age with a body mass index (BMI) of 18-25 kg/m$^2$, a resting blood pressure<140/90 mmHg, and habituated to—average caffeine consumption were considered eligible for inclusion in the study. Only right-handed subjects were included in the study to avoid spatial bias. Subjects had to refrain from caffeine products and vigorous physical activity 12 h prior to the study. As caffeine abstinence tends to increase sleepiness, consequently reducing the alertness score, the included subjects had to have an Epworth's sleeping scale≥10 indicating low mental alertness during general situations in day-to-day activities at screening and at all visits. The subjects had to refrain from smoking 24 h before study onset and refrain from alcohol intake throughout the study. Subjects with a history or presence of clinically important cardiac, renal, hepatic, endocrine (including diabetes mellitus), pulmonary, biliary, gastrointestinal, pancreatic, or neurological disorders and uncontrolled hypertension were excluded from the study. For each subject, the study was terminated after data collection on the assessment day.

Interventions

On day 1 of assessment, subjects were randomized in one of the arms to receive either the investigational product (IP), comparator (caffeine: CF), or the placebo. The IPs included *Cymbopogon flexuosus* (LG), water-soluble and water-insoluble extracts of *Alpinia galanga* (AG1 and AG2 respectively), and water-soluble and water-insoluble extracts of *Glycyrrhiza glabra* (GG1 and GG2 respectively). All interventions were administered to subjects in the form of identical capsules that had been packed in duly labeled HDPE bottles. The double-blinded nature of the study was ensured and strictly followed. All IPs were standardized for their activity, and the extracts were prepared by elimination of impurities using modern manufacturing techniques. The manufacture extracts and packaging of the finished product were carried out at a GMP-certified contract manufacturing facility in India. To maintain blinding, all the capsules were averaged to a weight of 500 mg. The composition details of all treatments are:

| Interventions | Ingredient | Quantity of active (mg/capsule) | Quantity of excipient (mg/capsule) | Total quantity (mg/capsule) |
|---|---|---|---|---|
| Placebo | Microcrystalline cellulose (MCC) | — | 500 | 500 |
| Caffeine (CF) | Anhydrous caffeine | 120 | 380 | 500 |
| LG | *Cymbogon flexuosus* essential oil from leaves | 148.75 | 351.25 | 500 |
| AG1 | *Alpinia galanga* water-soluble extract | 300 | 200 | 500 |
| AG2 | *Alpinia galanga* water-insoluble extract | 300 | 200 | 500 |
| GG1 | *Glycyrrhiza glabra* water-soluble extract | 500 | — | 500 |
| GG2 | *Glycyrrhiza glabra* water-insoluble extract | 500 | — | 500 |

Test Visit Procedure

On day 1 of the assessment, subjects reported to the clinic during the morning hours, and testing began at an early time of day (8:00-9:00 a.m.) for each visit to avoid influence of daily challenges (related to mental and physical stress) on outcomes. The time of day was matched for all visits to reduce variability due to the diurnal pattern. Subjects reported to the clinic after 24 hours of abstinence from caffeine and caffeine-containing products or any psychostimulants prior to all visits during the study. The subjects were also instructed to get sufficient sleep during the night prior to testing, which was self-reported by the participants in a sleep diary. Upon arrival at the clinic, subjects were asked to rest quietly for 15-20 minutes, after which physical examination was done, caffeine history was recorded, and the subjects were asked to fill out an Epworth's sleep scale questionnaire to rate their sleepiness. A standardized meal of approximately 200 calories was provided to control variations from possible digestion confounds. Baseline data on ANT was collected 30 minutes after breakfast followed by administration of the IP. Each dose consisted of two capsules of the product with a glass of water, which was administered to subject by the trial coordinator at the investigational site. After ingestion of IP, data were collected at 1, 3, and 5 hours and controlled for mean response time, alertness, orientation, and executive attention before and after IP administration. No other food or calorie-containing beverages were provided during the five-hour period. The subjects were allowed to drink water as desired and allowed to relax in an isolated room at a comfortable temperature and were free to use a computer, listen to music, or read magazines during the clinic stay period.

From days 2 to 6, participants were advised to take two capsules daily until day 6. On the day 7 visit, subjects followed the exact same schedule as that of day 1: after ingestion of two capsules, the subjects were allowed to rest for 30 minutes and last time point data were collected by ANT. To ensure treatment compliance, product accountability was monitored by a clinical research coordinator on the following visit.

Outcome Measures

The Attention Network Test (ANT) examines the effects of cues and targets within a single reaction time task in order to explore the efficiency of the alerting, orienting, and executive control networks of attention and mean response time with respect to different psychological and physiological states. It also provides an opportunity to examine the brain activity of these three networks as they operate in a single integrated task.

An adaptation of ANT, Centre for Research on Safe Driving Attention Network Task (CRSD-ANT), was used to evaluate the effect of IP on outcome measures.

Primary Efficacy Variables

CRSD-ANT was utilized to assess the effect of IPs on the mean response time (MRT) in milliseconds. Data were used to capture superiority within groups from baseline to each time point on the same day and intergroup comparisons.

Secondary Efficacy Variables

Effects of IPs on different aspects of the attention network, such as alertness, orientation, and executive control, were also assessed by ANT. These parameters are collectively responsible for achieving and maintaining vigilance and alertness while performing a continuous task.

Statistical Analysis

The sample size was calculated using PS: Power and Sample Size Calculation version 3.1.2 (2014). Continuous response variables were analyzed from matched pairs of subjects. In absence of prior data, an assumption was made that the difference in the response of matched pairs is normally distributed with a standard deviation of 2. Considering the mean response of matched pairs is two, at least eight subjects per arm were targeted to reject the null hypothesis that this response difference is zero with a probability (power) of 0.8. The Type I error probability associated with the test of this null hypothesis was 0.1.

All values are presented as means±standard deviation (SD). Statistical analyses were carried out on the data characterized by 95% confidence interval. Variables were tested for normality followed by student's paired t test for intergroup comparisons at different time points. p values of 0.05 were considered statistically significant.

Results:

70 subjects were recruited, of which 64 completed the study and 6 were withdrawn due to non-compliance. Analysis was performed on the intention to treat (ITT) population, which included subjects who were administered at least a single dose and for whom at least a single post-baseline assessment was available.

None of the treatment groups showed any significant reduction in response time at 1 h after IP administration. However, subjects in the LG group showed a significant increase in the MRT at 1 h (p=0.01), indicating delayed response. The caffeine group showed an improvement in the MRT at 3 h after IP administration (p=0.06), followed by a reversed trend in response time. The change in the response time in various groups is presented in FIG. 1. None of the treatment groups showed a significant effect on response time at 5 h after administration and after 7 days of exposure to IP.

Alertness

Figure 2:
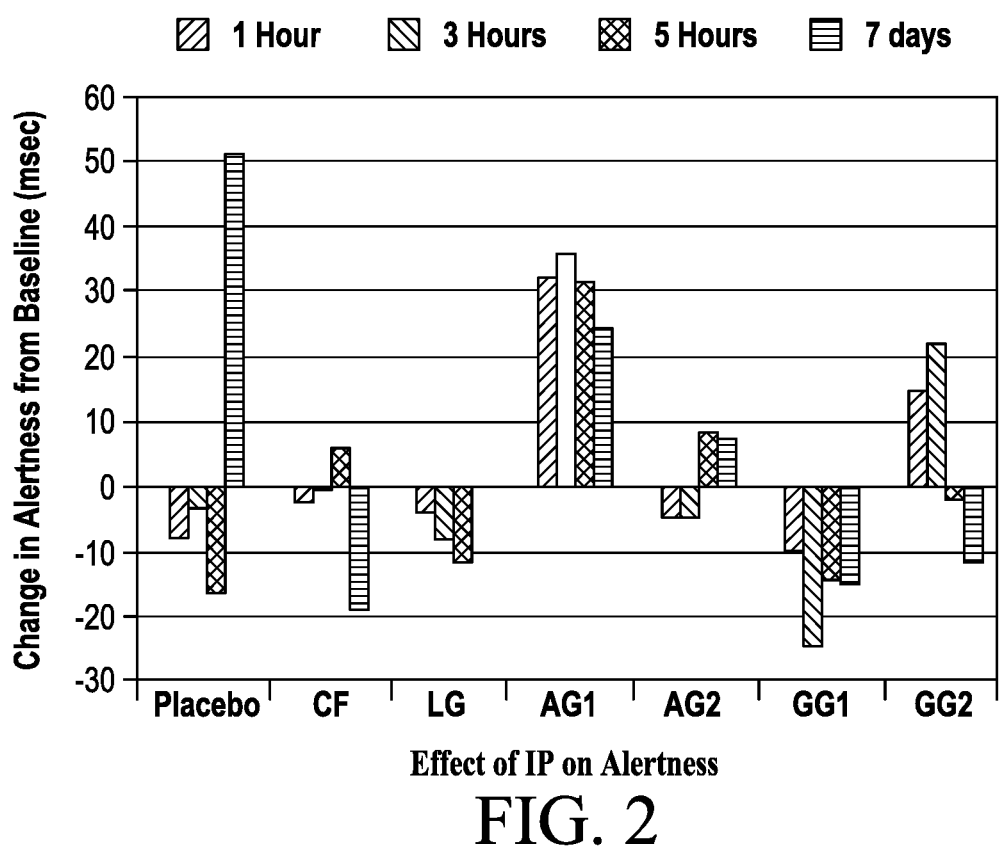
FIG. 2 shows an effect of *Alpinia galanga* that is free of methyl eugenol and other extracts on Alertness.

Among all the treatment groups, only the AG1 group showed a consistent improvement in the alertness time at 1 h (p=0.07) and 3 h (p=0.07) and achieved statistical significance at 5 h (p=0.007), which can be attributed to the reduction in the alertness score in placebo group at 5 h. However, the GG1 group exhibited a significant increase in alertness at 3 h, which slightly dropped at 5 h. Changes in the other groups were not as appreciable. FIG. 2 presents these data, revealing the superiority of the AG1 group in increasing alertness over the remaining groups. At day 7 after IP, the caffeine group exhibited a decrease in alertness compared to the placebo group (p=0.1). None of the treatment groups were effective in improving alertness at this point.

Orientation

None of the investigated IPs and the comparator demonstrated any significant effect on orientation compared to the baseline. At day 7 after administration of IP, none of the products demonstrated a better effect than placebo.

Executive Attention

None of the interventional groups showed any significant improvement in executive attention compared to placebo at 1, 3, and 5 hours after administration. At day 7, none of the groups showed significant effect on executive attention.

Discussion and Conclusion:

The above data were used to evaluate the efficacy and safety of natural product extracts in subjects with caffeine dependence. Several extracts were screened to elucidate the psychostimulant potential of the selected natural sources. Unlike studies which report findings on the basis of subjective feelings, these data were used to compare the effects of the IPs on different aspects of the attention network using the ANT, which is the only tool to independently analyze the different aspects of the attention network.

Although, change in caffeine group at 3 h did not reach statistical significance, it indicates caffeine's efficacy in reducing the mean response time, thus ascertaining its literature reported effect. This finding also validated the reliability of the ANT as an assessment tool for attention-related studies.

Among the extracts (LG, AG1, AG2, GG1, and GG2), AG1 showed a consistent improvement in alertness at 1, 3, and 5 h as compared to baseline and placebo. This can be attributed to the water-soluble compounds such as polyphenols, pyrocatecollic type tannins, and polysaccharides, abundantly present in *A. galanga*, which were skillfully extracted in the water-soluble extract.

The neurocognitive effect responsible for improving alertness (observed in the AG1 group) cannot be solely attributed to purine-like alkaloids such as caffeine or theacrine, as AG1 has a rich phytochemical profile in addition to alkaloids. Moreover, the polyphenols and flavonoids of AG1 may be helpful in combating the caffeine-like "crash."

Example 2: Effect of the Extract of *Alpinia galanga* that is Free of Methyl Eugenol as Compared to Caffeine and a Composite Data were collected to assess the stimulant effect of *A. galanga* that is free of methyl eugenol in healthy young volunteers on specific parameters related to attention network and sleep architecture using standardized tests and questionnaires.

The efficacy of the extract of *Alpinia galanga* that is free of methyl eugenol was analyzed with a principal objective of developing a safe alternative to caffeine for increasing mental alertness and decreasing mental fatigue. The data were used to assess the extract of *Alpinia galanga* that is free of methyl eugenol as a psycho-stimulant in healthy young volunteers using specific parameters related to important aspects of attention networks and using standardized tests and questionnaires.

Subjects and Methods

Subjects

Subjects were derived through multiple sources including a healthy volunteer's database and a consumer group's survey agency. The subjects were then screened. Subjects were 18-40 years old, male and female, healthy, did not consume alcohol, did not smoke, and had minimal computer literacy. All subjects were predominantly right handed with a history of moderate caffeine consumption (2-4 cups of caffeinated beverages per day). The caffeine history was taken to ensure that the participants were acquainted with caffeine's stimulant effect and were not caffeine-sensitive. The subjects with body mass index (BMI) between 18.50 and 25.00 kg/m2 and a resting blood pressure≤140/90 mm Hg were considered eligible. To avoid subjects with psychotic disorders such as anxiety, depression, ADD or ADHD, subjects with Generalized Anxiety Disorder Screening (GAD-7) score≥7 & Patient Health Questionnaire-9 (PHQ-9) score≥14 were excluded from the study. Subjects with alertness score (Jin Fan's Attention Network Test, version 1.3.0) of 50±20 milliseconds at screening visit were considered eligible. Concomitant therapy was strictly prohibited in order to exclude any significant effect on the results. All the subjects were instructed thoroughly on the investigation procedures.

Interventions

Subjects were randomized and allocated to interventional products in each visit, divided in four treatment arms based on randomization chart [SPSS version 10.0, IBM] and similar trend was followed for subsequent visits. The interventional products (IP) include: the *Alpinia galanga* extract that is free of methyl eugenol (E-AG-01), caffeine, a combination of the *Alpinia galanga* extract that is free of methyl eugenol with caffeine (Composite) and a placebo. All these treatments were administered to subjects in the form of capsules which were identical in appearance and packed in duly labeled HDPE bottles. The blinding codes were secured at the site in tamper-evident sealed envelopes with no access to the investigators. Thus, the double blind nature of the data were ensured and strictly followed. As subjects in one arm received a combination of caffeine and *A. galanga*, the subjects receiving solely *A. galanga* or caffeine or placebo were co-assigned to additional placebo capsule to achieve double dummy design. Composition details of all these IPs are:

| Ingredients | E-AG-01 (mg/Capsule) | Caffeine (mg/Capsule) | Placebo (mg/Capsule) |
|---|---|---|---|
| *Alpinia galanga* Extract that is free of Methyl Eugenol | 300 | — | — |
| Caffeine (Anhydrous) | — | 200 | — |
| Microcrystalline Cellulose (MCC) | 250 | 350 | 550 |
| Total | 550 | 550 | 500 |

Test Visit Procedure

Subjects reported to the clinic during the morning hours and testing began at early time of day (8:00-9:00 a.m.) for each visit to avoid influence of daily challenges (related to mental and physical stress) on outcomes and the time of day was matched for all three visits to reduce variability in response due to diurnal pattern. Subjects reported to the clinic following a 24 hours abstinence from caffeine and caffeine-containing products or any psycho-stimulants prior to all visits to the site. Subjects were also instructed to obtain sufficient sleep during the night prior to testing which was confirmed using sleep diary. Upon arrival at clinic, subjects were asked to rest quietly for 15-20 minutes after which vital parameters were measured and a standardized meal of approximately 200 calories was provided to control variations from possible digestion confounds. Baseline data were collected 30 minutes post breakfast followed by administration of IP, wherein one dose of the product was administered to subject by trial coordinator at investigational site.

Post ingestion of IP, data were collected at 1, 3, and 5 hours. No other food or calorie-containing beverages were provided. Subjects were allowed to drink water as desired. Subjects were allowed to relax in an isolated room at a comfortable temperature and free to use the computer, listen to music or read magazines during the clinic stay period. To analyze the effect on IP on sleep architecture, a second dose was supplied in a labeled bottle to be taken before dinner in the night of the same day and subjects were asked to record all the details pertaining to sleep quality and duration in sleep diary. To ensure treatment compliance, product accountability was monitored by clinical research coordinator on the following visit.

Outcome Measures

The data were used to elucidate investigational product's effect on various psychoactive measures in habitual caffeine consumers. Also, the likelihood of desired synergistic effect to reduce caffeine crash was explored by consuming the *Alpinia galanga* extract that is free of methyl eugenol and caffeine.

The primary efficacy variable was mental alertness. Alertness is defined as achieving and maintaining a state of high sensitivity to incoming stimuli. The Attention network test (ANT) was implemented for this purpose as it provides a behavioral measure of the efficiency of the different components of attention networks separately within a single task. The downloaded JAVA version of ANT 1.3.0 (Fan et al., 2002, 2005) was used to conduct the trial. The subject was seated in a silent and secluded room. All external distractions were avoided and subjects were asked to give complete attention to the task at hand. Mental alertness in ANT was calculated in terms of difference score quantified in milliseconds and calculated by subtracting average double-cue RTs from the no-cue RTs. Higher score indicates more efficient functioning of the alerting system.

The secondary efficacy variables, namely sustained attention [assessed by Psychomotor Vigilance Task (PVT)], mental fatigue [assessed by Karolinska Sleepiness Scale (KSS) Score], sustained wakefulness (assessed by sleep duration), and sleep pattern [assessed by Groningen's Sleep Quality Scale (SQS) and sleep diary], were also assessed.

The data were used to assess the effect of IP on mean response time using psychomotor vigilance test. A 10-minute computer-based PVT was performed. Subjects were asked to respond by clicking the mouse on first appearance of red colored digit on screen for the duration of 10 minutes. The mean MRT was calculated in milliseconds, which is the time a subject took to press the response button as soon as each stimulus appeared. Lower MRT thus indicates more efficient sustained attention.

Mental fatigue is an indicator of individual's mental or physical performance capability and can impair an individual's alertness and ability to perform a continuous task. The subjects were asked to complete a standardized Karolinska sleepiness scale (KSS) questionnaire for assessment of mental fatigue at first visit to site and then prior to all sessions of ANT and PVT. The questionnaire is a self-defined 10 grade KSS score scale where lower score implies low mental fatigue and higher alertness.

Wakefulness in terms of sleep quality was assessed by Groningen's sleep quality score questionnaire and sleep diary in which sleep quality was graded in the form of a score (SQS) on the scale of 0-14 score. Lower score on this scale indicates higher subjective quality of sleep and vice versa. Subject was asked to fill SQS at all visit to site. They were provided with a sleep diary to fill in the morning immediately on waking up and SQS on the day after IP administration at night. The effect of IP on wakefulness was also assessed by recording the duration of sleep between two assessment sessions. Subject were asked to start the stop watch before taking a nap and to stop it once they are awake or when they are woken up by the investigator for assessment. The stop watch was lapped and re-started if the subject wanted to nap again.

Power Calculation

The trial was designed to demonstrate efficacy of E-AG-01 over placebo. Internal unpublished data show at least 12±3% increase in alertness score in the active arm compared to placebo arm with a type I error ($\alpha$) of 5%. A sample size of 60 subjects was used to achieve 90% study power, accounting for dropouts &withdrawals (~20%) as well as non-evaluable subjects for the primary efficacy outcome (~25%).

Statistical Analysis

Statistical analysis was carried out using SPSS 15.0 for Windows (Chicago, Ill., USA). Variables were tested for normality using the Shapiro-Wilk test. The chi-square test and the student's unpaired t test were applied while comparing different groups of responders for different independent variables. The student's paired t-test was used for the inter-group comparisons at different time points. Multivariate analysis of variance (MANOVA) was used to evaluate the amongst group statistical significance. Further, a repeated two-way ANOVA was performed to investigate the difference in alertness score due to a time treatment interaction. The p value<0.05 was considered as statistically significant at 95% confidence level. The subjects who met all inclusion-exclusion criteria and received at least one dose of each investigational product were considered as "intent to treat" (ITT) population. However, as the neurobehavioral functioning is heavily masked by homeostatic drive for sleep and metabolism, the alertness score is expected to have interpersonal variability. Hence, final analysis was conducted on the per protocol (PP) population, wherein included subjects had baseline alertness score of 50±20 ms at each individual study visit and completed the study visit successfully. The data were segregated based on the four interventional groups before subjecting it to the statistical analyses and represented in a similar manner in the results section.

Continuous variables (age, height, weight and BMI) were summarized by the treatment group using a summary statistics (number of observations, mean and standard deviation). ANOVA was applied to prove the insignificance in demographic characteristics across the four groups. Data pertaining to PHQ-9 and GAD-7 parameters were also evaluated statistically by ANOVA for assessment of within group significance level.

The effect size was calculated by the "Cohen's d" method to determine a clinical relevance of the observed effects in case of statistically significant outcomes.

Results

Study Population 59 subjects met the protocol-defined inclusion-exclusion criteria and were enrolled. Six subjects out of 59 were dropped out, primarily due to consent withdrawal (4/6) or were lost to follow-up (2/6). Two of the withdrawals were attributed to safety concerns.

Further statistical analyses were performed on the data collected from Per Protocol (PP) and Intended to Treat (ITT) populations. PP group represents the subjects whose baseline alertness score matched with protocol specified screening criteria on each baseline alertness score and completed the study successfully. ITT group included the subjects who met all inclusion/exclusion criteria and received at least one dose of each investigational product. Only the results pertaining to PP group are presented and considered to obtain clinically significant outcomes.

Varying number of subjects for some efficacy parameters in PP group is accountable to discarded data for the subjects for whom baseline did not match to protocol specified inclusion-exclusion criteria. Hence, the corresponding data were excluded from the statistical analysis, which did not affect the minimum study power (90%).

All subjects were screened for demographic parameters (age, gender, height, weight and BMI) at screening visit to confirm compliance with the protocol. Analysis of demographic characteristics of all subjects confirmed that there was no significant standard deviation ($p>0.05$) among the treatment groups. Analysis of baseline characteristics of all subjects analyzed by PHQ-9 and GAD-7 questionnaires confirmed that none of the groups had PHQ-9 and GAD-7 scores beyond the specified range, assuring that none of the subjects was suffering from any mental disorders such as anxiety and depression. The groups did not differ statistically from each other ($p>0.05$) at screening.

Effect on Primary Outcome Measures

Figure 3:
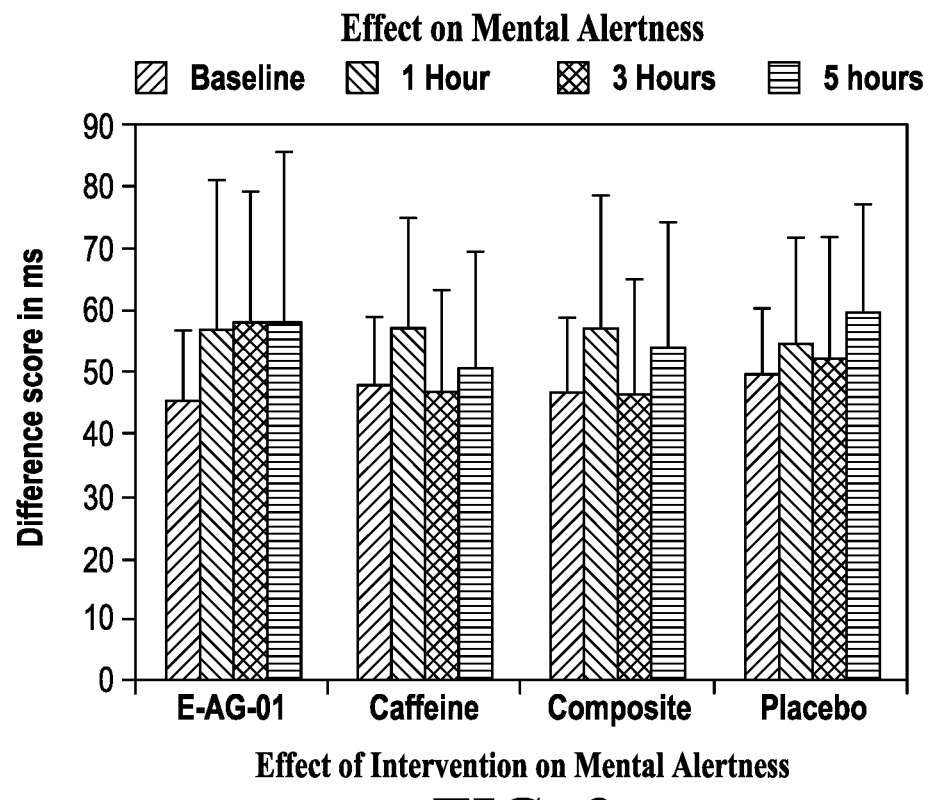
FIG. 3 shows an effect of *Alpinia galanga* that is free of methyl eugenol, as compared to caffeine, a composite of *Alpinia galanga* that is free of methyl eugenol and caffeine, and placebo on Mental Alertness.

Mental alertness was considered as primary outcome measure based on its importance in the assessment of cognitive performance. Data obtained for alerting network are expressed as alertness score in the following table and in FIG. 3:

| | ANT-Alertness (Mental Alertness) in Milliseconds (msec) | | | | |
|---|---|---|---|---|---|
| Variable | E-AG-01 (N = 34) | Caffeine (N = 35) | Composite (N = 38) | Placebo (N = 38) | p* |
| BL | 45.5 ± 11.2 | 48.0 ± 11.1 | 46.8 ± 12.0 | 49.63 ± 11.0 | 0.45 |
| 1H | 57.1 ± 23.8[#] | 57.0 ± 18.1[#] | 57.0 ± 21.7 | 54.7 ± 17.0[#] | 0.94 |
| 3H | 58.0 ± 21.2 | 46.8 ± 16.8 | 46.1 ± 19.1 | 52.2 ± 19.5[#] | 0.03[##] |
| 5H | 58.1 ± 27.6 | 50.8 ± 19.0 | 54.2 ± 20.3[#] | 59.4 ± 17.7[#] | 0.31 |

| Variable | E-AG-01 vs. Placebo | Caffeine vs. Placebo | Composite vs. Placebo |
|---|---|---|---|
| Intergroup Analysis by Student's Paired t test | | | |
| p (1H) | 0.20 | 0.38 | 0.26 |
| p (3H) | 0.04[###] | 0.40 | 0.50 |
| p (5H) | 0.59 | 0.11 | 0.64 |
| Repeated two-way ANOVA for Time X Treatment Interaction | | | |
| p (F) | 0.26 (1.42) | 0.73 (0.42) | 0.63 (0.58) |

Note:

*MANOVA test applied across 4 groups to get the p values,

**paired t test applied between two groups;

[#]Decreased significantly as compared to baseline;

[##]Statically significant difference in score across the groups;

[###]Significant change in score as compared to placebo,

BL: Baseline value;

1H: Value at 1 hour;

3H: Value at 3 hours;

5H: Value at 5 hours.

In the placebo group, there was a statistically insignificant increase in alertness score of 5.05±19.71, 2.61±20.66, and 9.79±20.07 ms from baseline at one, three and five hours, respectively.

In the E-AG-01 group, there was a significant increase in alertness score of 11.65±23.94 (95% CI: −3.67-16.86, p=0.008), 12.50±19.73 (95% CI: 0.37-19.42, p=0.001), and 12.62±24.71 (95% CI: −7.69-13.35, p=0.005) ms from baseline at one, three and five hours, respectively.

In the caffeine group, alertness score as compared to baseline increased significantly by 8.97±18.20 ms (95% CI: −4.96-12.80, p=0.006) at one hour; however, the score decreased by 1.23±18.60 ms (95% CI: −13.04-5.37, p=0.698) from the baseline at three hours, indicating a caffeine crash. Also, in composite group, the score significantly increased by 10.27±20.34 ms (95% CI: −4.96-12.80, p=0.004) from baseline at one hour followed by the return approximately to the baseline score with decrease of 0.68±21.87 (95% CI: −13.01 to 6.43, p=0.074) at three hours.

As the changes across the groups were significant at three hours (p=0.03), they were individually compared to the placebo using a student's paired t-test, wherein the E-AG-01 group demonstrated a statistically significant improvement in the alertness score (p=0.04).

At five hours, all groups demonstrated an increase in the alertness score, owing to the logistic factors of the study and asymptomatic performance improvement due to the diurnal pattern of the alertness, however the increase in the alertness score was maximum in the E-AG-01 group (12.62±0.68 ms from baseline).

As the result was statistically significant for E-AG-01, the effect size was calculated in terms of a Cohen's d value in comparison with placebo. The derived value of d=0.59 for the EAG-01 group as against d=0.08 for the caffeine group confirmed a significant medium effect size in alertness score in E-AG-01 group compared to a remarkably small effect size in caffeine group.

Effect on Secondary Outcome Measures

Figure 4:
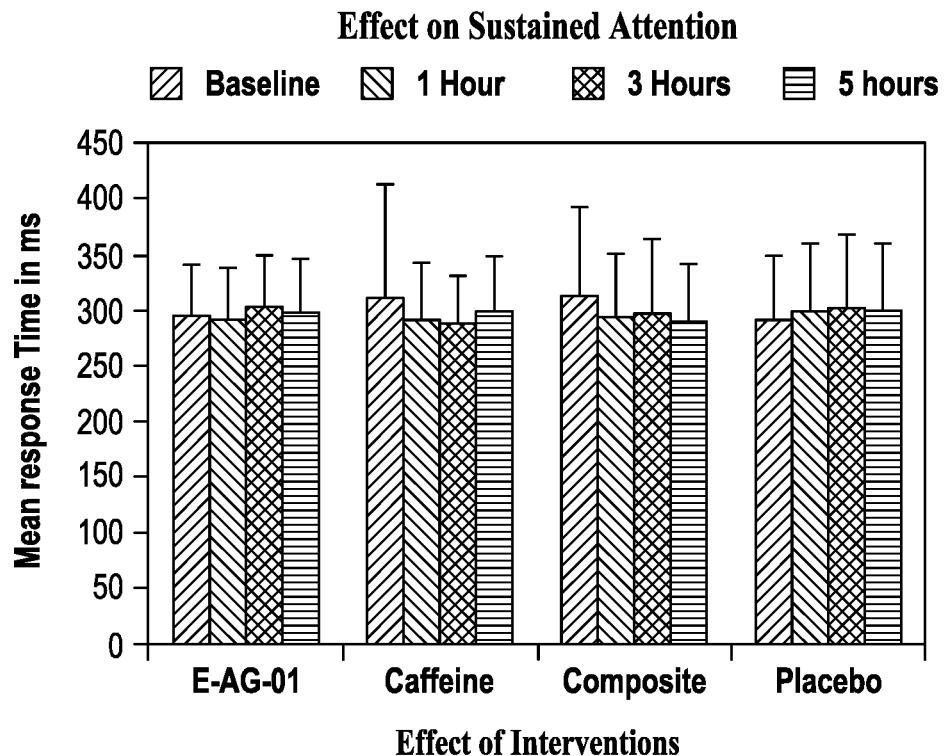
FIG. 4 shows an effect of *Alpinia galanga* that is free of methyl eugenol, as compared to caffeine, a composite of *Alpinia galanga* that is free of methyl eugenol and caffeine, and placebo on Sustained Attention.

The data were used to assess the effect of IP on the sustained attention by using the PVT and the results were expressed as MRT in msecs. As evident from the results, the E-AG-01 group did not demonstrate any significant improvement in the MRT whereas the results from the caffeine group suggested a declining trend in the MRT till 3 hours after which it showed an increase which may be attributed to the crash effect. The composite group exhibited a trend similar to the caffeine group but achieved a within-group statistical significance at 5 hours interval as compared to baseline (p=0.02). In addition, the intergroup analysis for the composite group revealed a significant decrease in MRT compared to the placebo at 1 hour (p=0.01), 3 hours (p=0.04) and 5 hours (p=0.01). The mean response time as computed by PVT is expressed in the following table and in FIG. 4:

| PVT-Mean Response Time (Sustained Attention) in Milliseconds (msec) | | | | | |
|---|---|---|---|---|---|
| Variable | E-AG-01 (N = 34) | Caffeine (N = 35) | Composite (N = 38) | Placebo (N = 38) | p* |
| BL | 292.7 ± 47.7 | 310.4 ± 103.3 | 311.6 ± 81.9 | 290.4 ± 59.0 | 0.50 |
| 1H | 290.2 ± 48.5 | 290.1 ± 51.6 | 292.7 ± 58.0 | 297.9 ± 62.6 | 0.92 |
| 3H | 299.5 ± 50.2 | 287.6 ± 43.1 | 296.0 ± 68.3 | 299.7 ± 67.8 | 0.82 |
| 5H | 297.1 ± 48.8 | 296.9 ± 51.5 | 288.7 ± 52.6 | 299.3 ± 60.3 | 0.84 |

| PVT-Mean Response Time (Sustained Attention) in Milliseconds (msec) | | | |
|---|---|---|---|
| Intergroup Analysis by Student's Paired t test | | | |
| Variable | E-AG-01 vs. Placebo | Caffeine vs. Placebo | Composite vs. Placebo |
| p (1H) | 0.13 | 0.09 | 0.01[##] |
| p (3H) | 0.73 | 0.06 | 0.04[##] |
| p (5H) | 0.60 | 0.17 | 0.01[##] |

Note:
*MANOVA test applied across 4 groups to get the p values,
**Student's paired t-test applied between two groups;
[#]Decreased significantly as compared to baseline;
[##]Significant change in score as compared to placebo,
BL: Baseline value;
1H: Value at 1 hour;
3H: Value at 3 hours;
5H: Value at 5 hours.

After the statistical evaluation and interpretation of the data obtained for the mental fatigue, it was found that none of the groups showed significant reduction in mental fatigue as assessed by KSS. Intergroup analysis also confirmed the statistically insignificant results in this outcome parameter. We also assessed the effect of IP on wakefulness and sleep quality and the results obtained for all four groups imply no statistically significant change in these outcome measures as well.

The data show the effect of an extract of *Alpinia galanga* that is free of methyl eugenol in comparison with the caffeine (comparator) and the placebo (control) on various aspects of attention network. Consistent with caffeine's well known effect on the alerting network, alertness score increased till one hour followed by a reduction, probably due to a caffeine crash at three hours. At the same time, the extracts of *Alpinia galanga* that is free of methyl eugenol showed an improvement in alertness score until five hours interval. In the composite group, alertness score increased significantly at one hour followed by a reduction, indicating a caffeine crash, which was less than that observed in the caffeine group. Hence, it can be hypothesized that the extract of *Alpinia galanga* that is free of methyl eugenol is able to impede the caffeine crash as evident from three hour and five hour alertness score.

The alerting network recruits a distributed network of brain regions, primarily the thalamus and bilateral frontal and parietal brain regions. Given the dense dopaminergic innervation of the human thalamus and prefrontal cortex and that the caffeine is generally thought to up regulate the dopaminergic availability, the present results are consistent with the theorized effects of caffeine on the CNS function. Based on these facts, it can be postulated that the extract of *Alpinia galanga* that is free of methyl eugenol also improves alertness in a similar way as that of caffeine by enhancing the dopaminergic activity.

The effect size for this efficacy parameter was calculated in terms of standardized mean effect, (denoted as Cohen's d) which expresses the mean difference between two groups in the standard deviation units. The results suggest that in terms of probability of superiority of treatments, there is a 66% chance that a randomly selected subject from the E-AG-01 group will exhibit a definite improvement in the mental alertness than a randomly selected subject from the placebo group.

Alternatively, it can be stated that the effect size represented as Cohen's d value indicates that 73% subjects from the E-AG-01 group (d=0.599) would exhibit higher alertness than the subjects in the placebo group as compared to the caffeine group wherein only 47% subjects would have a better alertness.

The sustained attention was assessed by the PVT, which generally reflects the arousal and attention state of an individual. Caffeine appears to exhibit dose-dependent performance improvement in a variety of basic psychomotor tasks as a direct result of altered CNS activity and is well reported by a number of studies. Some studies also suggest that the extended vigilance is generally improved following a caffeine consumption at a dose of ~400 mg and performance diminishes with very high dose of caffeine (e.g. 600 mg). In agreement with these reported findings, the data show that neither caffeine at 200 mg nor the extract of *Alpinia galanga* that is free of methyl eugenol at 300 mg independently exhibited significant reduction in the MRT. However, the combination of these ingredients at the same dose was found to be effective in improving the sustained attention as indicated by statistically significant data obtained for the composite group. It has been reported that the relationship between the sustained attention and the task performance follows an inverted U-curve, i.e. poor performance can occur due to both under- and over-arousal. This can be one of the reasons for wide-spread range of observations in MRT, leading to the bigger SDs and insignificant p values. However, derived p values showed a positive trend in the reduction of MRT in the caffeine and composite groups. Hence, an attempt was made to analyze the treatment groups individually in comparison with placebo by student's t-test which showed that the improvement in sustained attention was statistically significant in comparison with placebo, implying the superiority of the composite group in enhancing the sustained attention and arousal state. Thus, co-administration of the extract of *Alpinia galanga* that is free of methyl eugenol with caffeine may modulate the neural activity in the cerebral regions related to the sustained attention.

Within and between group analyses provided the statistically significant results, which serve as a constructive evidence for the beneficial effect of the extract of *Alpinia galanga* that is free of methyl eugenol on enhancement of mental alertness and sustained attention.

It should be apparent from the foregoing description that various embodiments of the disclosed formulation, extraction process, and use may be implemented to provide the various types of formulations described herein. The description further implements methods of administering an extract of *Alpinia galanga* that is free of methyl eugenol to improve cognitive performance as well as a process for preparing an extract of *Alpinia galanga* that is free of methyl eugenol.

Although the various embodiments have been described in detail with particular reference to certain aspects thereof, it should be understood that the disclosed formulation, extraction process, and use are capable of other embodiments and its details are capable of modifications in various obvious respects. As is readily apparent to those skilled in the art, variations and modifications can be affected while remaining within the spirit and scope of the disclosed formulation, extraction process, and use. Accordingly, the foregoing disclosure and description are for illustrative purposes only and do not in any way limit the disclosed formulation, extraction process, and use, which are defined only by the claims.

What is claimed is:

1. A method for improving cognitive performance in a human subject in need thereof, comprising:
    administering a formulation to the human subject, wherein the formulation comprises:
    100-900 mg of a water extract of *Alpinia galanga* that is free of methyl eugenol; and
    an ingestible carrier,
    thereby causing an improvement in cognitive performance,
    wherein the extract is soluble in a solvent selected from the group consisting of water, an alcohol, and a combination thereof.

2. The method of claim 1 wherein the improvement in cognitive performance is selected from the group consisting of improved mental alertness, increased attention, impeded caffeine crash, and combinations thereof.

3. The method of claim 1 wherein the extract of *Alpinia galanga* that is free of methyl eugenol includes a ratio of polyphenols to polysaccharides of about 1:1.6 to about 1:12.

4. The method of claim 1 wherein the extract of *Alpinia galanga* that is free of methyl eugenol includes 1% pyrocatecollic type tannins.

5. The method of claim 1 wherein the extract of *Alpinia galanga* that is free of methyl eugenol includes not more than 100 ppm galangin.

6. The method of claim 1 wherein the carrier is selected from the group consisting of microcrystalline cellulose, maltodextrin, and a combination thereof.

* * * * *